US00PP18238P3

(12) United States Plant Patent
Windham et al.

(10) Patent No.: US PP18,238 P3
(45) Date of Patent: Nov. 20, 2007

(54) DOGWOOD TREE NAMED 'APPALACHIAN JOY'

(50) Latin Name: ***Cornus florida* L.**
Varietal Denomination: Appalachian Joy

(75) Inventors: Alan S. Windham, Murfreesboro, TN (US); Mark T. Windham, Knoxville, TN (US); Robert N. Trigiano, Knoxville, TN (US)

(73) Assignee: University of Tennessee Research Foundation, Knoxville, TX (US)

( * ) Notice: Subject to any disclaimer, the term of this patent is extended or adjusted under 35 U.S.C. 154(b) by 5 days.

(21) Appl. No.: 11/315,478

(22) Filed: Dec. 22, 2005

(65) Prior Publication Data

US 2007/0150991 P1 Jun. 28, 2007

(51) Int. Cl.
*A01H 5/00* (2006.01)

(52) U.S. Cl. ..... Plt./220
(58) Field of Classification Search ..... Plt./220
See application file for complete search history.

(56) References Cited

U.S. PATENT DOCUMENTS

PP13,098 P2 10/2002 Windham et al.
PP13,099 P2 10/2002 Windham et al.
PP13,165 P2 11/2002 Windham et al.

OTHER PUBLICATIONS

Corley, C. "Dogwood Days, Again!" *Institute News,* Apr. 2006, pp. 1–6, http://agriculture.tennessee.edu/news/releases/0604–dogwood.htm, accessed on Apr. 13, 2006.
Corley, C. "Dogwood Days, Again!" *Institute News,* Apr. 2006, pp. 1 and 6, Third Thursday.

*Primary Examiner*—Kent Bell
(74) *Attorney, Agent, or Firm*—Saliwanchik, Lloyd & Saliwanchik

(57) ABSTRACT

A new distinct cultivar of dogwood, *Cornus florida* L., named 'Appalachian Joy', is provided. This cultivar is characterized by resistance to powdery mildew, which is superior to most other cultivars of flowering dogwood and similar to 'Karen's Appalachian Blush' (U.S. Plant Pat. No. 13,165 P2), 'Kay's Appalachian Mist' (U.S. Plant Pat. No. 13,098 P2) and 'Jean's Appalachian Snow' (U.S. Plant Pat. No. 13,099 P2). It also is characterized by producing supernumerary (multiple [4–8]) bracts.

2 Drawing Sheets

BACKGROUND OF THE INVENTION

The present invention relates to a new and distinct cultivar of flowering dogwood, which is resistant to powdery mildew and has supernumerary bracts. This dogwood is botanically known as *Cornus florida* L. and hereinafter referred to by the following cultivar name: 'Appalachian Joy'.

This new dogwood cultivar was discovered in a field planting of approximately 1,100,000 *C. florida* seedlings in Decherd, Tenn. in 1995. 'Appalachian Joy' is a supernumerary bracted (more than four bracts), white flowering dogwood, which, to the knowledge of the inventors, is superior to most other cultivars of flowering dogwood and similar to 'Karen's Appalachian Blush' (U.S. Plant Pat. No. 13,165 P2), 'Kay's Appalachian Mist' (U.S. Plant Pat. No. 13,098 P2) and 'Jean's Appalachian Snow' (U.S. Plant Pat. No. 13,099 P2) with respect to powdery mildew resistance. Asexual reproduction of 'Appalachian Joy' by terminal cuttings harvested at the Tennessee Agricultural Experiment Station in Knoxville, Tenn. and grafting of axillary buds onto seedling rootstocks have shown that the unique features of this new dogwood cultivar are stable and reproduced true-to-type in successive generations.

DETAILED DESCRIPTION OF THE NEW VARIETY

Figure 1:
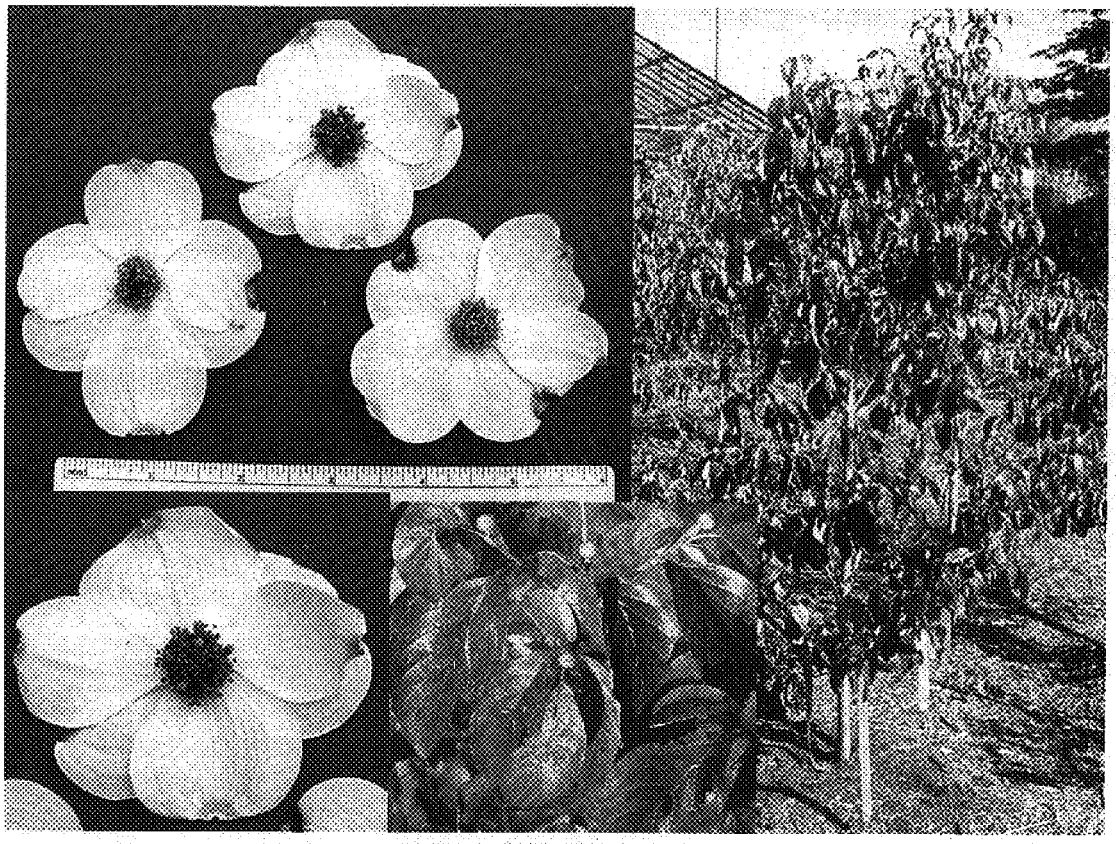
FIG. 1. Photograph of a typical inflorescences of 'Appalachian Joy' depicting supernumerary bracts, flower buds and fall color. Inflorescences, flower buds and fall foliage colors in the photograph may differ from the actual colors due to lighting and light reflectance.

The parental lineage of this cultivar is unknown. 'Appalachian Joy' is a white flowering dogwood cultivar with supernumerary bracts isolated from a field planting of approximately 1,100,000 *Cornus florida* seedlings in Decherd, Tenn. Seeds in this field were bulked from collections of wild and landscape trees growing in Tennessee, North Carolina, Alabama and Georgia. This cultivar may be reproduced asexually by rooted cuttings and by grafting axillary buds onto seedling rootstock.

'Appalachian Joy' has supernumerary white (Green-White Group 157 D: All color classifications are based on The Royal Horticultural Society's Colour Chart) bracts. The primary pairs of bracts slightly overlap and are wider (46 mm) than they are long (38 mm) (n=44). The greatest overall width of the inflorescences averages approximately 81 mm (n=38). The supernumerary bracts, when present, are on average about one-half the size of the primary bracts and range from 1 to 4. The number of bracts subtending receptacles ranges from 4 to 8 and averages about 5.6 (n=44). The clefts are Orange-Red (35 B) at the end of the bracts may be either flat or pointed and may or may not have deep Orange-Red (35 B) pigmentation. Flower petals are Yellow-Orange (14 B) with Red (42D) sepals and Yellow (13 D) anthers. There are about 23 flowers per inflorescence (n=44).

'Appalachian Joy' is a supernumerary bracted (more than four (4) and up to eight (8) bracts), white flowering dogwood, which, to the knowledge of the inventors, is superior to most other cultivars of flowering dogwood and similar to 'Karen's Appalachian Blush' (U.S. Plant Pat. No. 13,165 P2), 'Kay's Appalachian Mist' (U.S. Plant Pat. No. 13,098 P2) and 'Jean's Appalachian Snow' (U.S. Plant Pat. No. 13,099 P2) with respect to powdery mildew resistance. This cultivar has been rated for powdery mildew resistance for five (5) years. Ratings for the cultivars listed in Table 1 were obtained using the following scale: 0=healthy; 1=≦2% of foliage with signs or symptoms of powdery mildew; 2=≦10% of foliage with signs or symptoms of powdery mildew; 3=≦25% of foliage with signs or symptoms of powdery mildew; 4=≦50% of foliage with signs or symptoms of powdery mildew; 5=>50% of foliage with signs or symptoms of powdery mildew. A summary is provided in Tale 1 for 2002 through 2005 data collected at Ellington Agricultural Center, Nashville, Tenn.

TABLE 1

Comparison of Three Patented Flowering Dogwood Cultivars That are Powdery Mildew Resistance to 'Appalachian Joy' and Powdery Mildew Susceptible Cultivars.

| Cultivar | 2002 | 2003 | 2004 | 2005 |
|---|---|---|---|---|
| 'Jean's Appalachian Snow' | 0 | 0 | 0 | 0 |
| 'Karen's Appalachian Blush' | 0.7 | 0.7 | 0.3 | 0.3 |
| 'Kay's Appalachian Mist' | 0 | 0.3 | 0 | 0.3 |
| 'Appalachian Joy' | 0 | 0 | 0 | 0 |
| 'Cherokee Daybreak' or other susceptible white bracted flowering dogwoods | 4.3 | 5 | 5 | 4.7 |

DNA amplification fingerprinting (DAF) was used to type 'Appalachian Joy'. The methodology followed that of Trigiano and Caetano-Anolles (HortTechnology, 8:413–423 [1998]). Data, obtained from 144 loci generated from genomic DNA using six (6) arbitrary octomeric primers, were used to compare 'Appalachian Joy', the subject of his application, to other dogwoods including patented powdery mildew resistant cultivars ['Karen's Appalachian Blush' (U.S. Plant Pat. No. 13,165 P2), 'Kay's Appalachian Mist' (U.S. Plant Pat. No. 13,098 P2) and 'Jean's Appalachian Snow' (U.S. Plant Pat. No. 13,099 P2)] and other commonly found cultivars in nurseries, including *C. florida* 'Plena', which also exhibits supernumerary white bracts, but is sterile and *C. florida* 'Cherokee Brave', a red-bracted cultivar, which exhibits some resistance to powdery mildew. The sequence of the primers were the following (5' to 3'): GAG CCT GT; GAT CGC AG; GTA TCG CC; AAT GCA GC; CTA ACG CC; and GTA ACG CC. DAF as well as cluster analyses were completed using the NTSYS-pc program, version 2.2 (Exeter Software, 100 N. Country Road, Sedtauket, NT 11733). A similarity index is provided in FIG. 2 and FIG. 3 depicts the cluster analysis of the relationship between flowering dogwood cultivars.

Figures 2, 3:
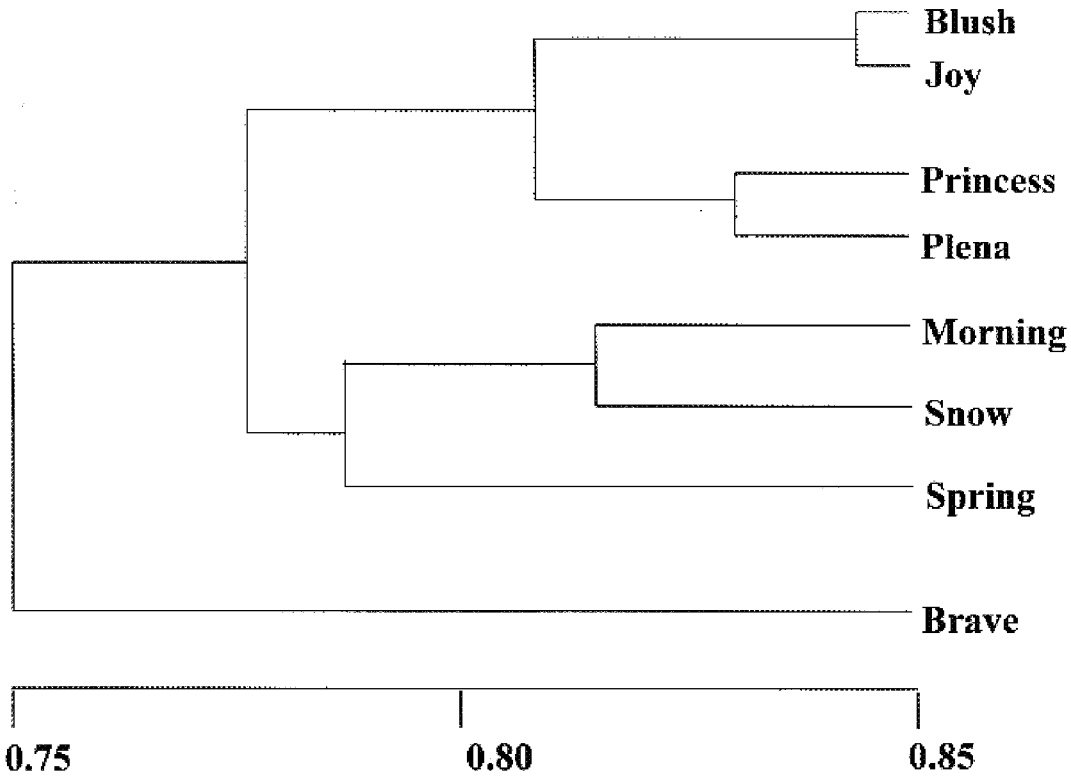
FIG. 2. A similarity index for various dogwoods.
FIG. 3. Cluster analysis of various dogwoods.

The abbreviation found in FIGS. 2 and 3 are as follows: Blush='Karen's Appalachian Blush'; Joy='Appalachian Joy'; Morning='Missy's Appalachian Morning'; Snow='Jean's Appalachian Snow'; Spring='Appalachian Spring'; Brave='Cherokee Brave'; Princess='Cherokee Princess'; and Plena='Plena'. All are white-bracted flowering dogwood cultivars except 'Cherokee Brave', which is red.

DETAILED BOTANICAL DESCRIPTION

The following observations, measurements and comparisons describe this cultivar grown in Oak Ridge and Nashville Tenn. Dogwoods used for this description were about seven (7) years old and planted on six-foot centers with other dogwoods. Plant hardiness is expected to be zones 5–9.

The following descriptions uses color references to The Royal Horticultural Society Colour Chart, except where general terms of ordinary dictionary significance are used. All color ratings were on adaxial surfaces. Ratings for abaxial surfaces were not obtained because reflected/refracted light, due to the density of pubescence on abaxial surfaces, made accurate color determinations difficult or impossible. Measurements are provided as a range with the middle value providing the average (lower limit<average value<upper limit).

Botanical classification: *Cornus florida* L., 'Appalachian Joy'.

Parentage: Unknown.

Propagation:

*Type.*—Terminal softwood cuttings.

*Time to initiate roots (in June).*—About 3–4 weeks at about 25–30° C.

*Rooting habit.*—Profuse from base of cutting.

*Rooting hormone.*—5,000–10,000 ppm; five (5) second quick dip of DIP 'N' GROW (1% IBA, 0.5%NAA) (Dip 'N' Grow, Inc., Clackamas, Oreg.).

*Intermittent mist.*—Six (6) seconds ever six (6) minutes.

*Light.*—30–50% shade cloth over propagation bench.

*Media.*—Peat-perlite.

Plant description:

*Plant form and growth habit.*—Perennial deciduous tree, mostly upright with more or less horizontal branching.

*Plant size.*—A five-to-seven (5–7) year old tree will attain a height of about 270 cm and a width of about 120 cm.

*Vigor.*—Similar to other *Cornus florida* cultivars.

*Branching habit.*—Moderate, branch crotch angles of about 20–40° to main trunk.

*Main stem/trunk description.*—Diameter: about 3.5 cm; bark texture: smooth; bark color: Brown 250 C.

*Lateral branch description.*—Branch angle of about 45° with a range of 40–52°.

Foliage description:

*Arrangement.*—Simple, opposite; leaves mostly crowded towards branch apices.

*Leaf blade length (cm).*—9.5<10.9<12.8 (n=5).

*Leaf blade width (cm).*—6.1<7.4<8.5 (n=5).

*Petiole length (cm).*—1.1<1.4<1.6 (n=5).

*Petiole diameter (mm).*—About 1.0<1.2<1.4 (n=5).

*Shape.*—Broadly ovate.

*Apex.*—Acuminate, leaf tips mostly flat.

*Base.*—Acute to cuneate, about 15% unequal.

*Margin.*—Entire, slightly undulate.

*Texture.*—Upper surface: nearly glaborous. Lower surface: leaf hairs profuse on veins and vein axils (u) — 15<25<36.

*Color.*—Yellow-green 146 C.

*Leaf vein arrangement.*—Six (6) pairs, mostly opposite. Petiole reflexed about 80° from the plane of the leaf.

*Bipolar trichomes.*—Upper surface — low density (u) 6<7.2<10. Lower surface (u) 6<9.8<14.

Flower description:

*Fragrance.*—None.

*Flower bud size.*—6.7 mm (widest diameter) (n=12). 5.0 mm (base to tip) (n=12).

*Shape of involucral bracts.*—Obovate/pandurate.

*Apex shape of involucral bracts.*—Cuneate. The margin of bracts is entire and the base of the bracts is inserted into the receptacle and appears to be flat or conforming to the receptacle.

*Number of bracts.*—4<5.6<8 (n=44).

*Natural flowering season.*—Typically first through last week in April.

*Inflorescence arrangement.*—The rigid primary pairs of bracts slightly overlap and are wider (46 mm) than they are long (38 mm) (n=44). The supernumerary bracts, when present, are on average about one-half the size of the primary bracts and range from 1 to 4.

*Inflorescence width* (*fully open*).—About 8.1 cm (n=38).

*Bracts.*—Bract dimensions (primary set): Bracts about 3.8 cm long and 4.6 cm wide. Supernumerary bracts are about one-half the size. Bracts are green-white (157 D) and clefts are pointed or flat develop and orange-red color (35 B). The floral disc is about 9.4 mm in diameter. Floral development is asynchronous with the inflorescence. Anthers are yellow (13 D) and average 1.2 mm in length. There are four (4) stamens.

*Sepals.*—The four (4) sepals are slightly reddish (42 D) (more with age). The four sepals are fused into an elongated cylinder approximately 2.4 mm in diameter. Individual sepals are entire and smooth culminating into an equal-sided point (acute apex). Each side of the point is approximately 0.8 mm. Each sepal from the base to the tip averages approximately 3.7 mm and is about 1.3 mm wide. n=20.

*Flower number.*—About 23 per inflorescence.

*Petal color.*—Light yellow-orange (14 B).

*Ovary.*—Bilocular with each locule have one (1) ovule.

Fruit description:

*Berry type.*—Drupe (about 14 mm×7 mm) aggregated on the receptacle. Typically, 1 to 8 berries per inflorescence.

*Berry color* (*when ripe in October*).—Deep red (45 A); flesh yellow-orange (21 A).

*Disease resistance.*—This cultivar is superior to most other cultivars of flowering dogwood and similar to 'Karen's Appalachian Blush' (U.S. Plant Pat. No. 13,165 P2), 'Kay's Appalachian Mist' (U.S. Plant Pat. No. 13,098 P2) and 'Jean's Appalachian Snow' (U.S. Plant Pat. No. 13,099 P2) with respect to powdery mildew resistance.

*Other unique attribute.*—This cultivar exhibits supernumerary bracts.

We claim:

1. A new and distinct cultivar of Dogwood, *Cornus florida* L., named 'APPALACHIAN JOY', as illustrated and described.

* * * * *

| | Blush | Joy | Morn | Snow | Spring | Brave | Princess | Plena |
|---|---|---|---|---|---|---|---|---|
| Blush | 1.00 | | | | | | | |
| Joy | 0.85 | 1.00 | | | | | | |
| Morn | 0.81 | 0.78 | 1.00 | | | | | |
| Snow | 0.80 | 0.82 | 0.81 | 1.00 | | | | |
| Spring | 0.79 | 0.74 | 0.80 | 0.76 | 1.00 | | | |
| Brave | 0.75 | 0.78 | 0.79 | 0.74 | 0.71 | 1.00 | | |
| Princess | 0.78 | 0.81 | 0.76 | 0.73 | 0.73 | 0.72 | 1.00 | |
| Plena | 0.85 | 0.78 | 0.80 | 0.75 | 0.75 | 0.78 | 0.84 | 1.00 |

UNITED STATES PATENT AND TRADEMARK OFFICE

CERTIFICATE OF CORRECTION

PATENT NO. : PP 18,238 P3 
APPLICATION NO. : 11/315478
DATED : November 20, 2007
INVENTOR(S) : Alan S. Windham, Mark T. Windham and Robert N. Trigiano It is certified that error appears in the above-identified patent and that said Letters Patent is hereby corrected as shown below:

Column 2,
Line 28, "at the end of the bracts" should read --and the end of the bracts--.

Column 3,
Table 1 heading, line 2, "Mildew Resistance" should read --Mildew Resistant--.
Line 43, "subject of his" should read --subject of this--.
Line 58, "Sedtauket, NT" should read --Setauket, NY--.

Column 4,
Line 7, "descriptions" should read --description--.

Column 6,
Line 9, "with each locule have one (1) ovule" should read --with each locule having one (1) ovule--.

Signed and Sealed this

Seventeenth Day of June, 2008

JON W. DUDAS
*Director of the United States Patent and Trademark Office*